(12) United States Patent
Reusch

(10) Patent No.: US 11,486,869 B2
(45) Date of Patent: Nov. 1, 2022

(54) HANDHELD DEVICE USING A LIGHT GUIDE AND METHOD FOR USE THEREOF FOR DETERMINING A PLANT STATUS

(71) Applicant: YARA INTERNATIONAL ASA, Oslo (NO)

(72) Inventor: Stefan Reusch, Dülmen (DE)

(73) Assignee: YARA INTERNATIONAL ASA, Oslo (NO)

( * ) Notice: Subject to any disclaimer, the term of this patent is extended or adjusted under 35 U.S.C. 154(b) by 183 days.

(21) Appl. No.: 16/758,887

(22) PCT Filed: Oct. 26, 2018

(86) PCT No.: PCT/EP2018/079447
§ 371 (c)(1),
(2) Date: Apr. 24, 2020

(87) PCT Pub. No.: WO2019/081729
PCT Pub. Date: May 2, 2019

(65) Prior Publication Data
US 2021/0382025 A1    Dec. 9, 2021

(30) Foreign Application Priority Data
Oct. 26, 2017   (EP) .................................. 17198659

(51) Int. Cl.
*G06K 9/00*    (2022.01)
*G01N 33/00*   (2006.01)
(Continued)

(52) U.S. Cl.
CPC ....... *G01N 33/0098* (2013.01); *G06T 7/0012* (2013.01); *G06T 7/80* (2017.01);
(Continued)

(58) Field of Classification Search
None
See application file for complete search history.

(56) References Cited

U.S. PATENT DOCUMENTS

| 9,075,008 B2 | 7/2015 | Holland |
| 2014/0267670 A1 | 9/2014 | Tipgunlakant et al. |

(Continued)

FOREIGN PATENT DOCUMENTS

| CN | 201311393 Y | 9/2009 |
| DE | 10149879 A1 | 4/2003 |

(Continued)

OTHER PUBLICATIONS

Vesali et al., "Feasibility of Using Smart Phones to Estimate Chlorophyll Content in Corn Plants", Photosynthetica 55 (4) 603-610, 2017.

(Continued)

*Primary Examiner* — Sean M Conner
(74) *Attorney, Agent, or Firm* — Dilworth IP, LLC

(57) ABSTRACT

The invention relates to a handheld device and method for determining a status of a plant. The device includes a multi pixel digital colour sensor, a light source arranged for providing broadband illumination, wherein the light source and the multi pixel digital colour sensor are arranged in substantially the same plane, a light guide for guiding the light from said light source into the direction of the multi pixel digital colour sensor, a sample space, provided between the multi pixel digital colour sensor and the light source, for insertion of at least a part of the plant therein, and a processing unit configured for controlling at least the multi pixel digital colour sensor and the light source.

21 Claims, 7 Drawing Sheets

(51) Int. Cl.
     *G06T 7/80*          (2017.01)
     *G06T 7/90*          (2017.01)
     *G06T 7/00*          (2017.01)

(52) U.S. Cl.
     CPC ...... *G06T 7/90* (2017.01); *G06T 2207/10024* (2013.01); *G06T 2207/10152* (2013.01)

(56) References Cited

U.S. PATENT DOCUMENTS

| | | |
|---|---|---|
| 2016/0231171 A1 | 8/2016 | Assefa et al. |
| 2016/0307040 A1* | 10/2016 | Shulman ................. G06K 9/22 |
| 2017/0131200 A1* | 5/2017 | Raveh .................... G01N 21/23 |
| 2018/0052088 A1* | 2/2018 | Sarkar ...................... G06T 7/20 |

FOREIGN PATENT DOCUMENTS

| | | |
|---|---|---|
| EP | 1429594 B1 | 1/2005 |
| EP | 1750106 A1 | 2/2007 |
| WO | 2003026383 A1 | 4/2003 |
| WO | 2015077493 A1 | 5/2015 |

OTHER PUBLICATIONS

International Search Report and Written Opinion, Application No. PCT/EP2018/079447, dated Mar. 8, 2019, 16 pages.
Extended European Search Report for 20212773.4; 10 pages, dated Feb. 17, 2021.
Chinese Office Action for App. No. CN201880069654.6, dated Nov. 25, 2021, 22 pages.

\* cited by examiner

HANDHELD DEVICE USING A LIGHT GUIDE AND METHOD FOR USE THEREOF FOR DETERMINING A PLANT STATUS

FIELD OF THE INVENTION

The invention relates to a device and a method for determining a plant status, more in particular a nutritional status of a plant.

BACKGROUND TO THE INVENTION

It is known to determine a plant status, such as a plant nutritional status, with the help of chlorophyll content. The chlorophyll content is usually determined by means of optical (e.g. reflectance or transmittance) measurements. However, devices for determining the plant status can be large, sophisticated, cumbersome to deploy, and/or expensive.

PRIOR ART

Vesali et al. in Photosynthetica 55, 2017 discloses a smartphone, adapted for use as an imaging spectrometer, to estimate chlorophyll content in corn plants. Background light source illumination was provided using a separate LED in front of the camera, providing constant illumination of the sample, arranged between the LED and the camera (light-aided spectral absorption photometry, LASAP, method).

WO 2015/077493 A1 (Digimarc Corporation, 28 May 2015) discloses a smartphone, adapted for use as an imaging spectrometer, by synchronized pulsing of different LED light sources as different image frames are captured by the phone's CMOS image sensor. A particular implementation employs the CIE colour matching functions, and/or their orthogonally transformed functions, to enable direct chromaticity capture. The spectral images are processed for use in object identification, classification, and a variety of other applications. Particular applications include produce (e.g., fruit or vegetable) identification.

U.S. Pat. No. 9,075,008 B2 (Kyle H. Holland, 3 Mar. 2011) discloses a method and system for treating a plant, comprising measuring optical properties of a plant using at last three spectral bands; calculating in a computational device at least two difference vegetative indexes using the optical properties, each of the at least two vegetative indexes correlating to one or more plant growth parameters; calculating in the computational device a water invariant chlorophyll index from the at least two difference vegetative indexes using the at least three spectral bands; and treating one or more of the plants based on the water invariant chlorophyll index.

EP 1429594 B1 (Norsk Hydro ASA, 3 Apr. 2003) discloses a method for determining and influencing the state of plants in a contactless manner, in particular the patch-specific or site-specific fertilizing of plants, in which the plants are illuminated by a modulated artificial halogen or xenon light source by means of a light spot or light strip during traversal with a carrier, the reflection signals of the foliage of the plants are captured in the visible and/or near-infrared spectral range by means of detectors and passed on to an evaluation and signal processing unit for determining biophysical parameters such as biomass, chlorophyll and/or water content and a measurement for the nutrition level of the plants is derived therefrom, which a computer uses to control the appropriate quantity of fertilizer to be applied as a target variable.

US 2016/0231171 A1 (Int. Business Machines Corp., 11 Aug. 2016) discloses a spectrometer apparatus comprising a mobile device including an integrated camera, having a camera lens and an image sensor. A detachable housing, comprising an optical spectrometer device and a closed sample space, can be coupled with the mobile device. A target image is processed by the optical spectrometer device and received by the image sensor. The mobile device may comprise a computer application to analyze the target image.

US 2014/0267670 A1 (Tipgunlakant, 18 Sep. 2014) discloses a mobile microscopy apparatus comprising an illumination module for illuminating a removable medium, such as a microscopy slide, to be inserted into a sample space which is closed during operation, an image acquisition optics and a mounting frame assembly. The microscopy apparatus is used with a mobile computing device comprising a memory unit and a camera to analyze a sample. The image acquisition unit creates a true image of the sample to be analyzed and the image is acquired by the camera. The illumination module may be the flash component of the camera comprised in the mobile computing device.

SUMMARY OF THE INVENTION

It is an objective to provide a simple, easy to use, easy to deploy, and/or inexpensive system. More in general, it is an objective to provide an improved system for determining a status of a plant.

According to an aspect is provided a handheld device for determining a status of a plant, in particular according to claim 1. The handheld device provides the advantage that the determination can easily be performed in situ, e.g. on the field.

The handheld device includes a multi pixel digital colour sensor and a light source arranged for providing broadband illumination, wherein the light source and the multi pixel digital colour sensor are arranged in substantially the same plane. Preferably, the light source and the multi pixel digital colour sensor are arranged along a vertical axis, one above the other. Preferably, the multi pixel digital colour sensor is positioned above the light source. Alternatively, the light source and the multi pixel digital colour sensor are arranged along an horizontal axis, one next to the other. The broadband illumination can e.g. be provided by a white light source, such as a white LED or a flash light. The multi pixel digital colour sensor can be any sensor known in the art, in particular comprising a sensor which has two or more, in particular 1 to 120 megapixels, and is able to measure one or more colour components. Preferably, the sensor is selected from a CMOS image sensor and a CCD image sensor. The sensor according to this invention will produce one or more readings, which, in this application, will be named an image. The readings may refer to the intensity measured for one or more colour components, to the intensity measured for one or more pixels, or to both. Optionally, the sensor may be provided with a lens in front of the sensor, in which case the sensor-and-lens arrangement can be called a camera.

The device further includes a light guide for guiding the light from said light source into the direction of said multi pixel digital colour sensor. The light guide comprises at least a light-emitting surface and a light-accepting surface and can have any shape. Optionally, and except for the light-emitting and light-accepting surfaces, the light guide is coated, covered, or shielded with a layer of a material. The layer of material can prevent ambient light from entering the light guide other than through the light-accepting surface and optionally light-emitting surface. The layer of material can prevent the light from the light source to exit the light guide other than through the light-emitting surface. Thus, the efficiency of the light guide can be increased. Optionally, the light guide includes a light diffusor. The light diffusor can aid in e.g. providing a substantially homogeneously light-emitting surface opposite the multi pixel digital colour sensor. The light diffusor can include a diffusively translucent surface, such as a frosted or matte surface. The light diffusor can include a diffusively translucent material, such as an opal glass or opal plastic. Optionally, the light guide is manufactured from a diffusively translucent material. The light guide may be a monolithic part.

The device further includes a sample space, provided between the multi pixel digital colour sensor and a portion of the light guide, for insertion of at least a part of the plant which status is to be determined, therein. A sample space for insertion of at least a part of a plant therein, can be provided between the light-emitting surface of the light guide and the multi pixel digital colour sensor, which are positioned on opposite sides of the sample space, e.g. directly opposite each other. An optical axis of the multi pixel digital colour sensor can extend through the light-emitting surface, e.g. substantially through a centre of the light-emitting surface. When a part of a plant, e.g. a leaf, is inserted into the sample space, the light source will transmit light subsequently through the light-accepting surface of the light guide, the light guide, the light-emitting surface of the light guide, and the plant part, onto the multi pixel digital colour sensor. The sample space is an open sample space, in contact with ambient air and light, when in use. The sample space can be a slit so as to allow easy insertion of a leaf, while allowing for a small distance, of e.g. 2 mm or less, between the multi pixel digital colour sensor and the light-emitting surface of the light guide.

Alternatively, or additionally, a sample space for insertion of at least a part of a plant therein, is provided between the light source and the light-accepting surface of the light guide, which are positioned on opposite sides of the sample space, e.g. directly opposite each other. An optical axis of the light source can extend through the light-accepting surface, e.g. substantially through a centre of the light-accepting surface. When a part of a plant, e.g. a leaf, is inserted in the sample space, the light source will transmit light subsequently through the plant part, the light-accepting surface of the light guide, the light guide and the light-emitting surface of the light guide, onto the multi pixel digital colour sensor. The sample space can be a slit so as to allow easy insertion of a leaf, while allowing for a small distance, of e.g. 2 mm or less, between the light source and the light-accepting surface of the light guide.

Optionally, the sample space is open in such a way that it allows the insertion of an unprocessed part of a plant which status is to be determined. The handheld device may be used directly on the plant in a field. The part of the plant to be analysed, e.g. a leaf, does not need to be cut or separated from the plant. It may be cleaned to obtain a more reliable and accurate measurement.

Preferably, the space between the multi pixel colour sensor and the portion of the light guide should be free from any other optical equipment, such as lenses, mirrors, prisms, gratings.

The device further includes a processing unit configured for controlling at least the multi pixel digital colour sensor and the light source. The processing unit can be configured for controlling the multi pixel digital colour sensor and the light sensor for obtaining at least a colour reading, such as a colour image, of the part of the plant inserted into the sample space. Optionally, the processing unit can also be configured for performing mathematical calculations, as explained below.

Preferably, the handheld device is a computational and/or communication device, such as a smartphone, a laptop or a tablet. The multi pixel digital colour sensor can then be part of a camera of the smartphone, laptop or tablet.

Optionally, the light source can be a light source, such as a flash light, of the handheld device. Thus, the handheld device can advantageously use a camera and light source generally available on a handheld device, such as a smartphone or a tablet. The light guide can provide that a light-emitting surface of the light guide, and hence of the entire light source, is positioned opposite the camera lens, and hence the multi pixel digital colour sensor. Hence, in a mechanically simple and effective manner, the handheld device can be transformed for allowing detection of light transmission through the plant part.

Optionally, the light guide is detachably attached to the handheld device, e.g. by means of a clip, clamp, adhesive or the like. Optionally, the light guide is part of a cover of the handheld device. The light-accepting surface of the light guide should at least partially overly the light source of the handheld device. The light guide should at least partially overhang the multi pixel digital colour sensor (or camera) of the handheld device.

Optionally, the processing unit is configured for controlling the multi pixel digital colour sensor and for switching the light source on and off, and configured for obtaining a first image with the light source switched on, and obtaining a second image with the light source switched off. It will be appreciated that the order in which the first and second image are obtained may vary.

Optionally, the multi pixel digital colour sensor is configured for obtaining a colour image, e.g. of the plant part in the sample space. It will be appreciated that such image does not need to be a focused image since the plant part in the sample space may be very close to the camera lens. The colour image includes pixels, each of which comprises at least a red (R), green (G) and blue (B) colour component, together forming a set of colour components.

The processing unit is configured for determining a first colour value representative of a difference in intensity values in the first and the second image for a first of the colour components. In the case of a multi-pixel sensor, the reading will be an image. Optionally, the processing unit is configured for determining a second colour value representative of a difference in intensity values in the first and the second image for a second of the colour components. The processing unit can be configured for calculating a value representative of a status of the plants using the first colour value and the second colour value.

Determining the value representative of a status of the plant on the basis of the first image, i.e. with illumination by the light source (index ON), and the second image, i.e. without illumination by the light source (index OFF) provides the advantage that effects of ambient lighting conditions can be suppressed. Hence, reliability of the device is greatly enhanced. Also reproducibility of the determination can be enhanced. It will be appreciated that, in general, the device and method can be used for determining a value, representative of a status S of an object, such as a plant, root, leaf, petal, seed, flower, skin, etc.

The processing unit can be configured for calculating the value representative of the status of the plant by determining the first colour value as the difference of the pixel-averaged intensity value (i.e. the intensity value averaged over all pixels for the given colour component) in the first image and in the second image for the first of the colour components; determining the second colour value as the difference of the pixel-averaged intensity value (i.e. the intensity value averaged over all pixels for the given colour component) in the first and in the second image for the second of the colour components; and calculating the value representative of the status of the plant using the first colour value and the second colour value. Hence, the value, S, representative of the status of the plant is a function, $f$, of the average intensity value, $\overline{I_{1,ON}}$, in the first image and, $\overline{I_{1,OFF}}$, in the second image for the first of the colour components and of the average intensity value, $\overline{I_{2,ON}}$, in the first and, $\overline{I_{2,OFF}}$, in the second image for the second of the colour components:

$$S = f((\overline{I_{1,ON}} - \overline{I_{1,OFF}}), (\overline{I_{2,ON}} - \overline{I_{2,OFF}})) \qquad \text{EQ1}$$

Here, the first colour value is $V_1 = (\overline{I_{1,ON}} - \overline{I_{1,OFF}})$, and the second colour value is $V_2 = (\overline{I_{2,ON}} - \overline{I_{2,OFF}})$.

Because of the close distance to the camera for a standard handheld device, such as a smartphone, laptop or tablet, the leaf is most likely not in focus and the spatial distribution of the intensity values generally does not provide any information. Therefore, the use of average intensity values for the image can be justified.

The processing unit can be configured for calculating the value representative of the status of the plant by determining the first colour value as the difference in intensity values in the first and the second image for the first of the colour components per pixel; determining the second colour value as the difference in intensity values in the first and the second image for the second of the colour components per pixel; and calculating the value representative of the status of the plant by averaging a pixel-wise value representative of the status of the plant obtained using the first colour value per pixel and the second colour value per pixel. Hence, the value, S, representative of the status of the plant is a function, $f$, of the intensity value, $I_{1,ON,i}$, per pixel, i, in the first image and, $I_{1,OFF,i}$, in the second image for the first of the colour components and of intensity value, $I_{2,ON,i}$, per pixel in the first and, $I_{2,OFF,i}$, in the second image:

$$S_i = f((I_{1,ON,i} - I_{1,OFF,i}), (I_{2,ON,i} - I_{2,OFF,i}))$$

$$S = \frac{1}{n} \sum_{i=1}^{n} S_i. \qquad \text{EQ4}$$

Here the first colour value is $V_{1,i} = (I_{1,ON,i} - I_{1,OFF,i})$ for the $i^{th}$ pixel, and the second colour value is $V_{2,i} = (I_{2,ON,i} - I_{2,OFF,i})$ for the $i^{th}$ pixel.

The above ways of calculating the value representative of the status of the plant can also be used for each of a plurality of blocks of pixels of the first and second image. An eventual value, representative of the status of the plant, can be calculated by averaging such block-wise values representative of the status of the plant obtained.

Optionally, the processing unit is configured for, in step (iii), calculating the value, S, representative of the status of the plant based on a ratio of the first colour value and the second colour value. Hence, S can be denoted as $S = V_1/V_2$. Herein $V_1$, and $V_2$ can be determined as above.

The processing unit can, for instance, be configured for calculating the value, S, representative of the status of the plant as:

$$S = \frac{\overline{I_{1,ON}} - \overline{I_{1,OFF}}}{\overline{I_{2,ON}} - \overline{I_{2,OFF}}} \qquad \text{EQ5}$$

wherein $\overline{I_{1,ON}}$ is a first colour component intensity value, averaged over a plurality of pixels of the first image, $\overline{I_{1,OFF}}$ is a first colour component intensity value, averaged over a plurality of pixels of the second image, $\overline{I_{2,ON}}$ is a second colour component intensity value, averaged over a plurality of pixels of the first image, and $\overline{I_{2,OFF}}$ is a second colour component intensity value, averaged over a plurality of pixels of the second image.

The processing unit can, for instance, be configured for calculating the value, S, representative of the status of the plant as $$S = \frac{1}{n} \sum_{i=1}^{n} \frac{I_{1,ON,i} - I_{1,OFF,i}}{I_{2,ON,i} - I_{2,OFF,i}} \qquad \text{EQ6}$$

wherein $I_{1,ON,i}$ is a first colour component intensity value for an $i^{th}$ pixel of the first image, $I_{1,OFF,i}$ is a first colour component intensity value for the $i^{th}$ pixel of the second image, $I_{2,ON,i}$ is a second colour component intensity value for the $i^{th}$ pixel of the first image, and $I_{2,OFF,i}$ is a second colour component intensity value for the $i^{th}$ pixel of the second image, and n is the number of pixels.

There is a relationship between leaf greenness and plant nitrogen status. Hence, plant nitrogen requirements can be determined based on measurement data collected from the plant leaves. Leaves of plants with increased levels of nitrogen typically have more chlorophyll and greater rates of photosynthesis. Hence, plants that appear a darker green are perceived to be healthier than nitrogen deficient plants. Hence, it is possible to sense or measure leaf greenness and obtain an indication of chlorophyll concentration and plant nitrogen status.

Furthermore, also other properties, representative of a plant status may be monitored, based on the disclosed colour method, and for this, appropriate colour values should be determined and a value representative of a status of the plant should be calculated.

Optionally, the first of the colour components is green (G) and the second of the colour components is red (R).

Since the intensity of the green colour component and the red colour component can be dependent on a thickness of the plant part in the sample space, using the ratio of the green image component and the red image component can also be used to make the measurement result, i.e. the ratio, less dependent from plant part thickness.

Optionally, the processing unit is further configured for determining a third colour value representative of a difference in intensity values in the first and the second image for a third of the colour components, and calculating the value representative of the status of the plant using the first colour value, the second colour value, and the third colour value.

It will be appreciated that the third colour value can be determined as the difference of the average intensity value in the first image and in the second image for the third of the colour components or as the difference in intensity values in the first and the second image for the third of the colour components per pixel.

Optionally, the processing unit is configured for, in step (iii), calculating the value representative of the status of the plants based on a ratio of the first colour value and the second colour value, e.g. as in EQ5 or EQ6. Using a ratio of two colour values allows to calculate a value representative of a plant status wherein sensitivity for the first colour value is increased by using the second colour value as reference.

Optionally, the processing unit is configured for, in step (iii), calculating said value representative of the status of the plants based on a hue value using the first, second and third colour value. The hue value $h_{RGB}$ can be conventionally calculated as $$h_{RGB} = \text{atan } 2(\sqrt{3}/(V_G-V_B), 2V_R-V_G-V_B) \quad \text{EQ7}$$

wherein $V_R$ is the first colour value, wherein red is chosen as the first of the colour components, $V_G$ is the second colour value, wherein green is chosen as the second of the colour components, and $V_B$ is the third colour value wherein blue is chosen as the third of the colour components. The function atan 2 is the arctangent function with two arguments. For any real number arguments x and y not both equal to zero, atan 2(y,x) is the angle in radians between the positive x-axis of a plane and the point given by the coordinates (x,y) on it. The hue value can be representative of chlorophyll content. A darker green may indicate a higher chlorophyll content, a lighter green may indicate a lower chlorophyll content. A lighter green may indicate a nitrogen deficiency. The hue value can also be representative of other plant status.

The value representative of the status of the plant can also be determined as other mathematical combination of the first, second, and optionally third colour values, $V_1$, $V_2$ and $V_3$. For example, $S=(V_1-V_2)/(V_1+V_2)$, $S=(V_1-V_2)/V_3$, $S=V_1/(V_2-V_3)$, etc. or other parameters, such as hue and saturation can be calculated. In order for the value S to be insensitive to the absolute intensity of the light, preferably a ratio of colour values is used.

Optionally, the processing unit is configured for calibrating the first colour value, second colour value, and optional third colour value. This provides the advantage that deviations of the relative sensitivity of the colour channels, as typically occur between different sensors, different light guides and different mechanical setups, can be accounted for. Also, deviations in light intensity across the light-emitting surface of the light source may be accounted for.

Calibration can include obtaining, with the multi pixel digital colour sensor, a first reference image of a reference object with a, preferably known, uniform transmittance while the light source illuminates the reference object with the broadband illumination, and obtaining a second reference image of the reference object while the light source does not illuminate the reference object. The first reference image may also be obtained by taking an image without any object present in the sample space while the light source is switched on, and the second reference image may be obtained by taking an image without any object present in the sample space while the light source is switched off.

The processing unit can be configured for calibrating the first, second or third colour value by for that colour value multiplying the colour value by a calibration value, C, determined as a reference value, K, divided by the difference of the average intensity value $\overline{I_{C,ON}}$ in the first reference image and the average intensity value $\overline{I_{C,OFF}}$ in the second reference image for that colour component:

$$C = \frac{K}{\overline{I_{C,ON}} - \overline{I_{C,OFF}}}. \quad \text{EQ10}$$

The processing unit can be configured for calibrating the first, second or third colour value by for that colour value per pixel multiplying the colour value by a calibration value, $C_i$ determined as a reference value, K, divided by the difference in intensity values in the first reference image and the second reference image for the that colour component per pixel:

$$C_i = \frac{K}{I_{C,ON,i} - I_{C,OFF,i}}. \quad \text{EQ10}$$

Herein $I_{C,ON,i}$ is the intensity value for that colour component for an $i^{th}$ pixel of the first reference image, and $I_{C,OFF,i}$ is the intensity value for that colour component for the $i^{th}$ pixel of the second reference image.

The processing unit can be configured for calibrating the first, second or third colour value by per block, b, of pixels for that colour value multiplying the colour value by a calibration value, $C_b$, determined as a reference value, K, divided by an average of the difference in intensity values per pixel in the first reference image and the second reference image for that colour component:

$$C_b = \frac{K}{\frac{1}{p}\sum_{i=1}^{p}(I_{C,ON,i} - I_{C,OFF,i})}. \quad \text{EQ11}$$

Herein $I_{C,ON,i}$ is the intensity value for that colour component for an $i^{th}$ pixel of the first reference image, $I_{C,OFF,i}$ is the intensity value for that colour component for the $i^{th}$ pixel of the second reference image, and p is the number of pixels in the block.

The reference value, K, can be a constant, such as a maximum possible intensity value, a maximum intensity value encountered in the first reference image for that colour component, a maximum difference in average intensity values in the first reference image and the second reference image for that colour component, etc. The reference value, K, can represent the transmittance of the reference object at the respective colour component.

It will be appreciated that in case the processing unit calculates the value representative of the status of the plant based on a ratio of the first colour value and the second colour value, that the reference values K for the calibration constant $C_1$ for the first colour value and the calibration constant $C_2$ for the second colour value may disappear from the equation, e.g. if the reference value K is the same for all colour components. For example, when using the calibrated form of equation EQ5:

$$S = \left(\frac{\overline{I_{1,ON}} - \overline{I_{1,OFF}}}{\overline{I_{2,ON}} - \overline{I_{2,OFF}}}\right) \cdot \left(\frac{\overline{I_{C,2,ON}} - \overline{I_{C,2,OFF}}}{\overline{I_{C,1,ON}} - \overline{I_{C,1,OFF}}}\right) \quad \text{EQ12}$$

With $\overline{I_{C,1,ON}}$ the average intensity value in the first reference image for the first of the colour components, etc.

Optionally, the processing unit is configured for selecting and using at least one colour component that is less sensitive to changes in the plant status than the other of the colour components.

Optionally, the processing unit is configured for, in step (iii), calculating a value representative of a colour status of an object, using the intensity of one or more of the colour components.

Optionally, the processing unit is configured for controlling the multi pixel digital colour sensor and the light source for obtaining the first and second image in response to a single user command. Hence, a single user command starts a measurement sequence in which both the first and second image are automatically obtained. Preferably, the first and second image are obtained in fast succession. The first and second image can e.g. be obtained within 1 second, preferably within <100 ms, more preferably within <10 ms. Hence, measurement errors due to changes of the ambient light are reduced. For example, an exposure time of the multi pixel digital colour sensor can be 1/5000 s (200 µs), and a delay time between the first and second image can e.g. be 100 ms.

According to an aspect, the multi pixel digital colour sensor is configured for determining a red intensity value, a green intensity value and a blue intensity value. The multi pixel digital colour sensor can be an RGB digital colour camera of a handheld device such as a smartphone or a tablet. The green image component can be the green pixel values for the pixels in the image. The red image component can be the red pixel values for the pixels in the image.

According to an aspect the processing unit is configured for determining the value representative of a status of the plant, as a green/red ratio G/R, as:

$$G/R = 100 * \left( \frac{G_1 - G_0}{R_1 - R_0} * C - 1 \right).$$ EQ13

Herein $G_1$ is a first average green intensity value for a plurality of pixels of the first image, and $G_0$ is a second average green intensity value for a plurality of pixels of the second image. Herein $R_1$ is a first average red intensity value for a plurality of pixels of the first image, and $R_0$ is a second average red intensity value for a plurality of pixels of the second image. C is a calibration constant. It will be appreciated that $G_1$, $G_0$, $R_1$ and $R_0$ preferably relate to the same plurality of pixels. The plurality of pixels can be a predetermined area within the images, e.g. a centre area. The plurality of pixels can be a variable area within the images, e.g. an area with intensity values higher than a threshold value. The plurality of pixels can be all pixels within the images.

The calibration constant C can be determined by obtaining a first reference image with no object inserted into the sample space while the light source illuminates the multi pixel digital colour sensor with broadband illumination, and obtaining a second reference image with the light source being switched off. The calibration constant can be defined as:

$$C = \frac{Rr_1 - Rr_0}{Gr_1 - Gr_0}.$$ EQ14

Herein $Gr_1$ is a first average green intensity value for a plurality of pixels of the first reference image, and $Gr_0$ is a second average green intensity value for a plurality of pixels of the second reference image. Herein, $Rr_1$ is a first average red intensity value for a plurality of pixels of the first reference image, and $Rr_0$ is a second average red intensity value for a plurality of pixels of the second reference image. The calibration constant can e.g. compensate for multi pixel digital colour sensor-specific, light-guide-specific and/or light-source specific offsets of the device.

It will be appreciated that it is possible that the calibration constant, as defined hereinabove, is determined only once for a device. However, when the device is suspect of degradation, e.g. due to component degradation or contamination, the calibration constant may be determined anew. It will be appreciated that in this setup, a calibration is very simple (just take an "empty" reading). Therefore, in practice, the calibration step could simply be carried out once after power-on or after starting the software.

According to an aspect, the device further comprises a communications unit configured for communicating the determined status of the plant, or a parameter derived therefrom, to an applicator system, such as a fertilizer system, watering system, ventilating system, heating system, or the like.

Optionally, the device includes a position determination unit, such as a GPS unit, for determining location information of the device. The device can then be configured to store the status of the plant, or a parameter derived therefrom, in combination with the location information. Alternatively, or additionally, the device can be configured for communicating the determined status of the plant, or a parameter derived therefrom, in combination with the location information to an applicator system, e.g. a variable rate applicator system, such as a variable rate fertilizer system. Hence, the use of fertilizers may be reduced by precisely applying agricultural products to individual plants or locations to be treated.

According to an aspect, the device includes a smartphone, laptop or tablet. The multi pixel digital colour sensor, light source, processing unit and optional communications unit and position determination unit can be part of the smartphone, laptop or tablet. This provides the advantage that a compact device can be provided in a simple manner.

According to an aspect, a computer program product for determining a status of a plant is provided. The computer program product includes software code portions configured for, when executed on a programmable device, assisting a user, in need of determining the status of a plant, in response to a single used command to obtain a first image of a part, such as a leaf, of the plant with a multi pixel digital colour sensor of the device while a light source of the device transmits broadband illumination through the plant part, obtain a second image of the plant part with the multi pixel digital colour sensor while the light source does not illuminate the plant part, the first and second images comprising at least a red (R), green (G) and blue (B) colour component, together forming a set of colour components, determine a first colour value representative of a difference in intensity values in the first and the second image for a first of the colour components, determine a second colour value representative of a difference in intensity values in the first and the second image for a second of the colour components, and calculate a value representative of a status of the plant using the first colour value and the second colour value. Optionally, the computer program product is included in a non-transitory data storage device. The computer program product can e.g. be an app for the smartphone, laptop or tablet. Optionally, the app can be downloaded from a communications network, such as the internet.

According to an aspect, a combination of a casing and a token for obtaining and/or enabling said computer program product is provided. The token can be e.g. an indication of a location where to download the computer program product, such as a URL. The token can be an authorization code for authorizing download and/or use of the computer program product (e.g. enabling the program product to operate, or fully operate), e.g. from an app-store.

According to an aspect a method for determining a status of a plant using a device including a multi pixel digital colour sensor, a light source arranged for providing broadband illumination into the multi pixel digital colour sensor, a light guide for guiding the light from said light source into the direction of the multi pixel digital colour sensor, a sample space, provided between the multi pixel digital colour sensor and the light source, for insertion of at least a part of the plant therein, and a processing unit is provided. The method includes obtaining a first image of a part of a plant, inserted into the sample space, with the multi pixel digital colour sensor while the light source transmits broadband illumination through the plant part into the multi pixel digital colour sensor. The method includes obtaining a second image of the plant part, inserted into the sample space, with the multi pixel digital colour sensor, while the light source does not illuminate the plant part. The first and second images comprise at least a red (R), green (G) and blue (B) colour component, together forming a set of colour components. The method includes determining a first colour value representative of a difference in intensity values in the first and the second image for a first of the colour components. The method includes determining a second colour value representative of a difference in intensity values in the first and the second image for a second of the colour components. The method includes calculating a value representative of a status of the plant using the first colour value and the second colour value. The method preferably is a computer-implemented method.

Optionally, the method includes taking an action, such as watering, fertilizing, harvesting, shielding (e.g. from the sun), ventilating, and/or heating, in response to the calculated value representative of a status of the plant. The method can include providing an instruction to an operator or a machine for taking such action. The method can include comparing the value representative of a status of the plant with a threshold value or with a reference function, so as to determine whether or not to take the action.

It will be appreciated that any of the aspects, features and options described in view of the device apply equally to the method, computer program product and combination and vice versa. It will also be clear that any one or more of the above aspects, features and options can be combined.

BRIEF DESCRIPTION OF THE DRAWING

The invention will further be elucidated on the basis of exemplary embodiments which are represented in a drawing. The exemplary embodiments are given by way of non-limitative illustration. It is noted that the figures are only schematic representations of embodiments of the invention that are given by way of non-limiting example.

In the drawing.

DETAILED DESCRIPTION

Figure 1A:
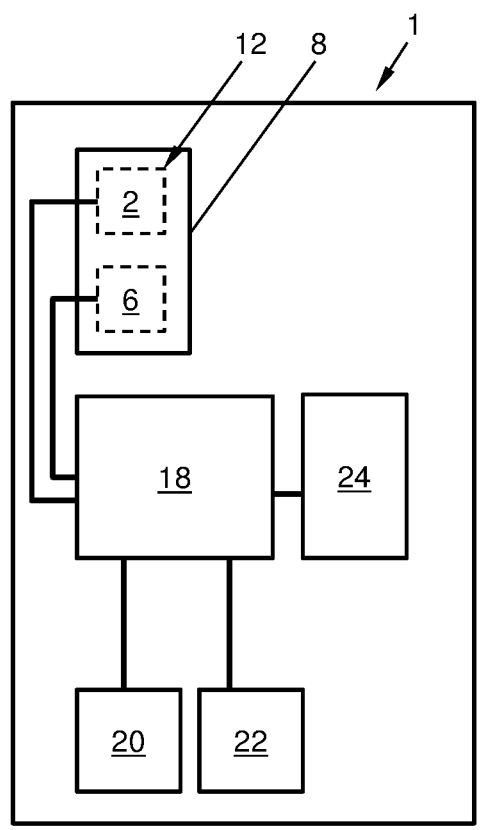
FIGS. 1A, 1B and 1C show a schematic representation of a device, respectively a front view, a rear view and a side view.
Figure 1B:
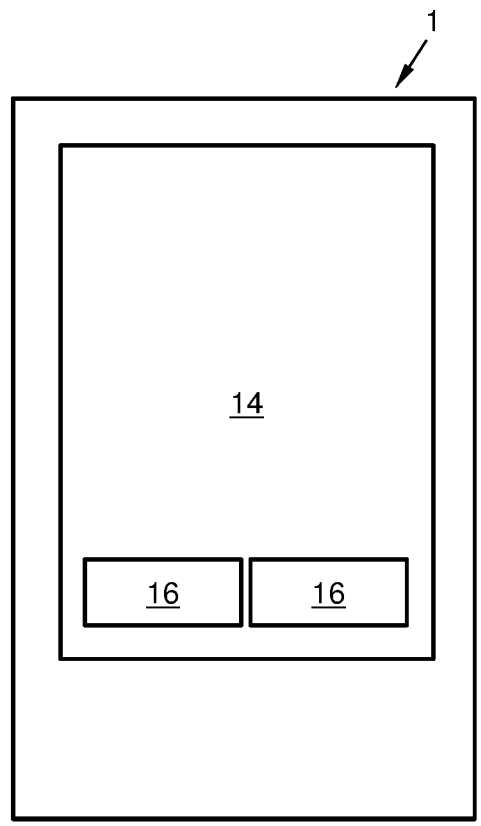
Figure 1C:
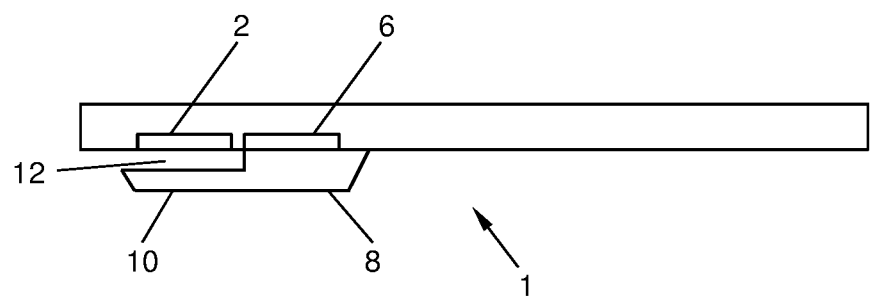
Figure 2A:
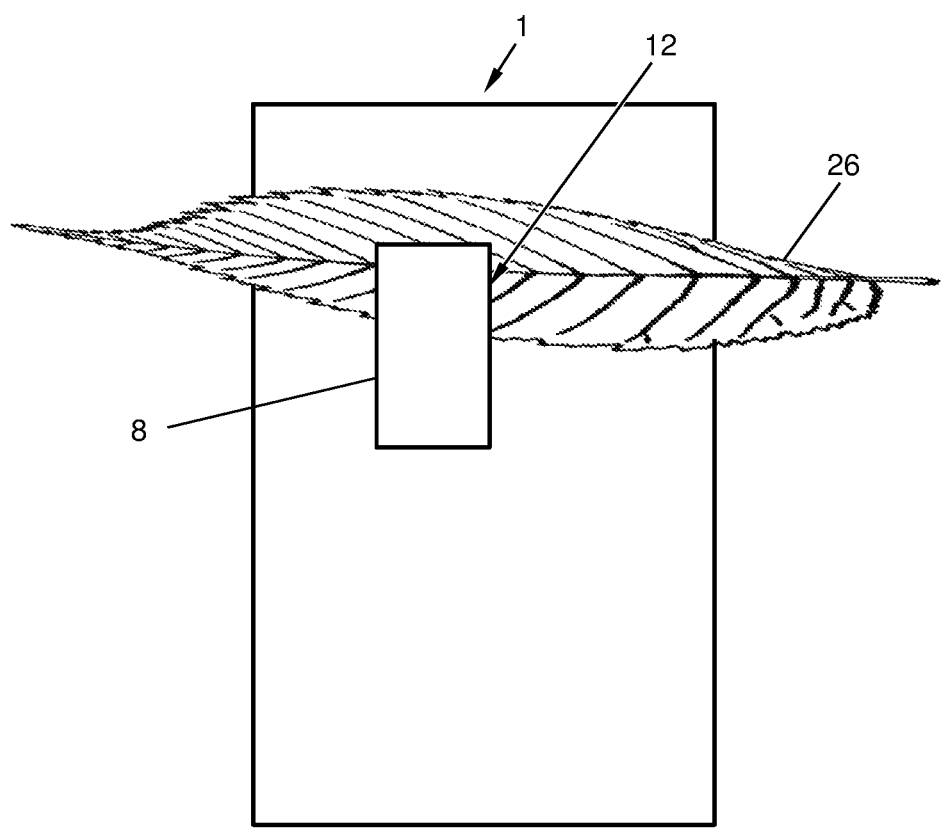
FIGS. 2A, 2B and 2C shows a schematic representation of a device, respectively a front view, a rear view and a side view.
Figure 2B:
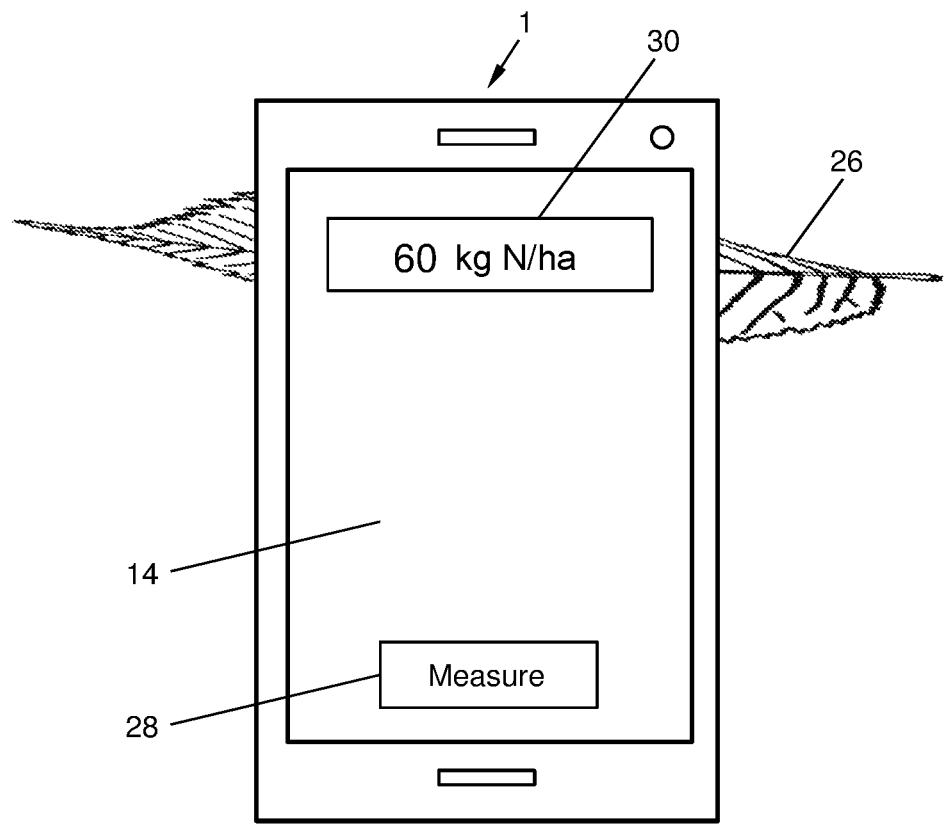
Figure 2C:
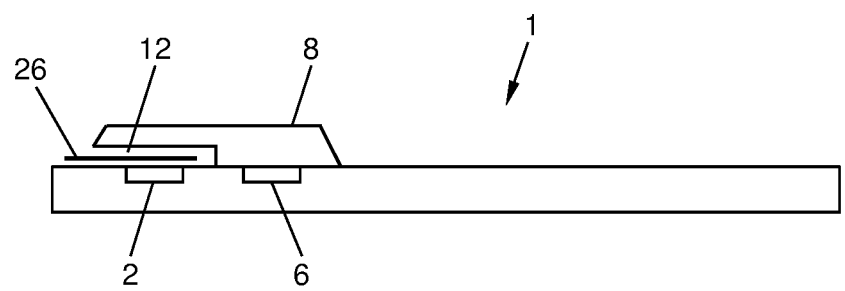

FIGS. 1A, 1B and 1C show a schematic representation of a, here handheld, device 1. In this example, the device 1 is a smartphone. FIG. 1A shows a front view of the device 1. FIG. 1B shows a rear view of the device 1. FIG. 1C shows a side view of the device 1. The device 1 includes a camera 2, comprising a multi pixel digital colour sensor and a lens, and a light source 6. The camera 2 is a colour camera. In this example, the camera 2 is an RGB camera. The RGB camera obtains images containing a plurality of pixels. For each pixel in the image, the camera 2 determines a red intensity value, a green intensity value and a blue intensity value. In this example, the camera provides 10-bit uncalibrated raw intensity values for each pixel and each colour channel. The output of such a camera is linearly related to light intensity.

In this example the light source 6 is a white light emitting diode, LED. Here, the light source 6 is placed below the camera 2.

In this example, the device 1 includes a light guide 8. The light guide 8 is positioned to receive light emitted by the light source 6. The light guide 8 guides light emitted by the light source 6 to be directed into the field of view of camera 2, i.e. the multi pixel digital colour sensor. In this example, a portion 10 of the light guide 8 is positioned opposite the camera 2. Between the portion 10 and the camera 2, a sample space 12 is formed. Into the sample space 12, a part of a plant, e.g. a part of a leaf, can be inserted. Here, the sample space forms a slit. The distance between the camera 2 and the portion 10 can be approximately 3 mm or less, e.g. about 2 mm or less.

As shown in FIG. 1B, the device 1 includes a user interface 14. Here, the user interface 14 includes a touch screen. The user interface includes, among others, controls 16 for controlling, such as triggering, the camera 2 and the light source 6.

In this example, the device 1 includes a processing unit 18. The processing unit is communicatively connected to the camera 2, the light source 6 and the user interface 14. Here, the device includes a communications unit 20. The communications unit 20 is communicatively connected to the processing unit 18. In this example, the device 1 includes a position determination unit 22, here a global positioning system, GPS, unit. The position determination unit 22 is communicatively connected to the processing unit 18. In this example, the device 1 includes a memory 24, suitable for storing a computer program, images, etc.

The device 1 as described so far, can be used as follows. Before the device 1 is used for determining a plant status, the device 1 can be calibrated. Thereto, the sample space 12 is simply left empty. Alternatively, a reference object of known and preferably spectrally uniform transmittance is inserted into the sample space 12. Via the user interface 14 a calibration measurement sequence can be started, e.g. by pressing a "calibrate" button on the touch screen. After activation of the calibration measurement sequence, the processing unit 18 instructs the light source 6 to switch on (if it is off) and instructs the camera 2 to take a first reference image. Next, the processing unit 18 instructs the light source 6 to switch off and instructs the camera 2 to take a second reference image. The first and second reference images can be, e.g. temporarily, stored in the memory 24 of the device 1. It will be appreciated that it is also possible that the second reference image (with light source off) is obtained before the first reference image is obtained (with light source on).

In this example, the processing unit 18 determines an average intensity value $Gr_1 = \overline{I_{G,ON}}$ for all green pixel intensity values of the first reference image. Next, the processing unit 18 determines an average intensity value $Gr_0=\overline{I_{G,OFF}}$ for all green pixel intensity values of the second reference image. In this example, the processing unit 18 determines an average intensity value $Rr_1=\overline{I_{R,ON}}$ for all red pixel intensity values of the first reference image. In this example, the processing unit 18 determines an average intensity value $Rr_0=\overline{I_{R,OFF}}$ for all red pixel intensity values of the second reference image. It will be appreciated that it is also possible that the processing unit 18 determines an average intensity value $Br_1=\overline{I_{B,ON}}$ for all blue pixel intensity values of the first reference image, and an average intensity value $Br_0=\overline{I_{B,OFF}}$ for all blue pixel intensity values of the second reference image.

Then, a calibration constant C is calculated using equation EQ15:

$$C = \frac{Rr_1 - Rr_0}{Gr_1 - Gr_0} \qquad \text{EQ15}$$

Referring now to FIGS. 2A, 2B, 3 and 6, a measurement is described. A plant part 26, here a part of a leaf, is inserted into the sample space 12. Via the user interface 14 a measurement sequence is started, e.g. by pressing a button 28 on the touch screen. After activation of the measurement sequence, the processing unit 18 instructs the light source 6 to switch on and instructs the camera 2 to take a first image of the plant part 26. Next, the processing unit 18 instructs the light source 6 to switch off and instructs the camera 2 to take a second image of the plant part 26. It will be appreciated that it is also possible that the second image is obtained before the first image is obtained. The first and second image can be, e.g. temporarily, stored in the memory 24 of the device 1. It will be appreciated that since the plant part 26 is positioned close to the camera 2, e.g. touching or almost touching the lens of the camera, the first and second images may be out of focus.

Here, the processing unit 18 automatically causes the device to take the two images in response to a single user command. The processing unit 18 causes the two images to be taken in fast succession. In this example the images are taken with an exposure time of 1/5000 s (200 μs) and a delay time between the images of 100 ms. The light source 6 is activated to be on during a period that is equal to or longer than the exposure time.

In this example, the processing unit 18 determines an average intensity value $G_1$ for all green pixel intensity values of the first image. In this example, the processing unit 18 determines an average intensity value $G_0$ for all green pixel intensity values of the second image. In this example, the processing unit 18 determines an average intensity value $R_1$ for all red pixel intensity values of the first image. In this example, the processing unit 18 determines an average intensity value $R_0$ for all red pixel intensity values of the second image.

Then, a value representative of a status of the plant is calculated. In this example, a spectral index, herein called FCCI (Flash Cam Chlorophyll Index), is calculated. Thereto a measured FCCI, is determined using equation 16:

$$FCCI' = 100 * \left( \frac{G_1 - G_0}{R_1 - R_0} * C - 1 \right) \qquad \text{EQ16}$$

The measured FCCI' value can be corrected with correction factor $K_D$. The correction factor can be device dependent. The correction factor can e. g. be representative of an empirically determined relationship between the FCCI' value determined by the processing unit 18 and an FCCI determined using a reference device. If no correction is needed, the correction factor can be equal to one (1).

$$FCCI = FCCI' \cdot K_D \qquad \text{EQ17}$$

This FCCI value is representative of the average greenness of the plant part 26. The device 1 can show the determined value to the user, e.g. on the user interface.

It is also possible that the device 1 indicates information representative of the value on the user interface. It is also possible that the processing unit performs an agronomic calibration on the basis of the value representative of the status of the plant. In this example, the processing unit 18 determines a recommended amount of nitrogen (N) to be supplied to the plants as a function of the determined FCCI (e.g. as kg N per ha). The N-recommendation can e.g. be displayed in a field 30 of the user interface.

It will be appreciated that the FCCI value calculated according to equation EQ17 is only one example of a plant status. More in general, the device can determine a plant status, such as a plant nutritional status, on the basis of various mathematical combinations of the available (i. e. R, G and B) colour values. For example, the processing unit 18 can determine a hue value on the basis of all three colour values.

In this example, the device 1 stores information representative of the determined FCCI value in a record in the memory 24.

In this example, the geographical position determination unit 22 determines a geographical position of the device 1 during the measurement. Information representative of the geographical position is stored in the record with the information representative of the determined FCCI value. The record can be stored for access and analysis.

Alternatively, or additionally, the device 1 can transmit the determined status of the plants, or a parameter derived therefrom, e.g. in combination with the location information to an applicator system, e.g. a variable rate applicator system, such as a variable rate fertilizer system, using the communication unit 20. The applicator system can then adjust the rate of fertilizer application to the received status information. Hence, the use of fertilizers may be optimized, e.g. reduced, by precisely applying agricultural products to individual plants or locations to be treated.

In the example of FIGS. 1A, 1B, 1C, 2A, 2B and 2C, the device is embodied as a smartphone. The smartphone includes the camera 2, light source 6, light guide 8, processing unit 18, communications unit 20 and position determination unit 22. The light source 6 can e.g. be a flash light of the smartphone. In this example, the smartphone is provided with dedicated software, such as an app, enabling the smartphone to perform the functionality as described hereinabove.

Figure 3:
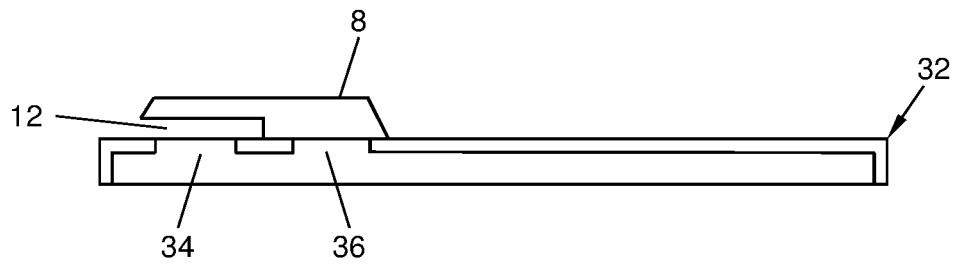
FIG. 3 shows a schematic representation of a casing for fitting to a device.

In the example of FIG. 3, the light guide 8 is included in a casing 32 for the smartphone. FIG. 3 shows an example of a cross sectional view of such casing 32. The casing is arranged for being attached to the smartphone, e.g. by clicking. In this example, the casing 32 includes a first aperture 34 for exposing the camera 2 to light from the light-emitting surface of the light guide 8. In this example, the casing 32 includes a second aperture 36 for exposing the light guide 8 to light emitted by the light source 6. In this example, the light guide 8 is attached to the casing 32, e. g.

by clicking, welding, gluing or the like. It is also possible that the light guide is a unitary part of the casing. The casing 32 can be provided as a separate add-on unit for converting the smartphone to the device 1 with the light guide. It is also possible that the light guide 8 is attached or attachable to the smartphone.

Optionally, the casing or light guide is provided in combination with a token. The token allows the dedicated software to be installed and/or used on the smartphone. The token can e.g. include an indication of a location, such as a URL, where the dedicated software can be downloaded. The location can be a secure location. The token can e.g. include an authentication allowing the location to be reached and/or allowing the dedicated software to be downloaded and/or installed, and/or allowing the software to be executed on the.

Figure 4A:
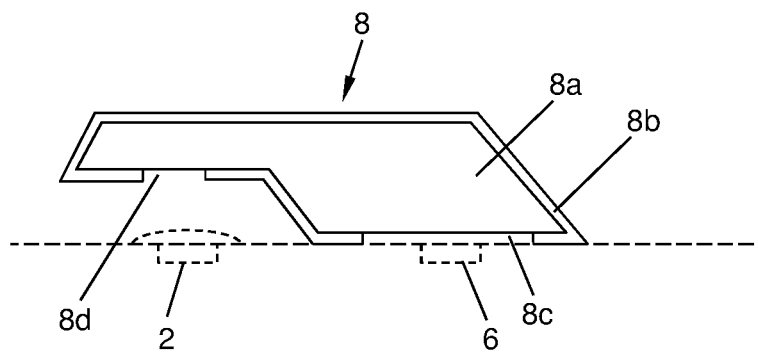
FIGS. 4A and 4B show a schematic representation of a light guide, respectively a side view and a bottom view.
Figure 4B:
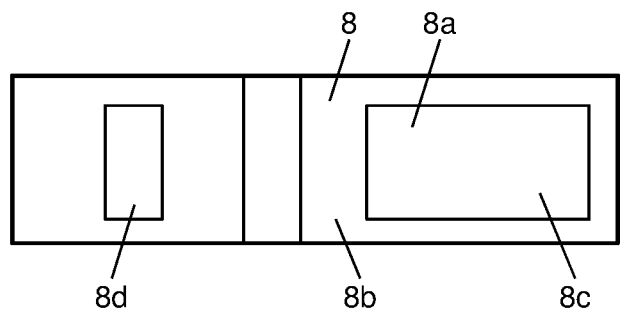
Figure 5:
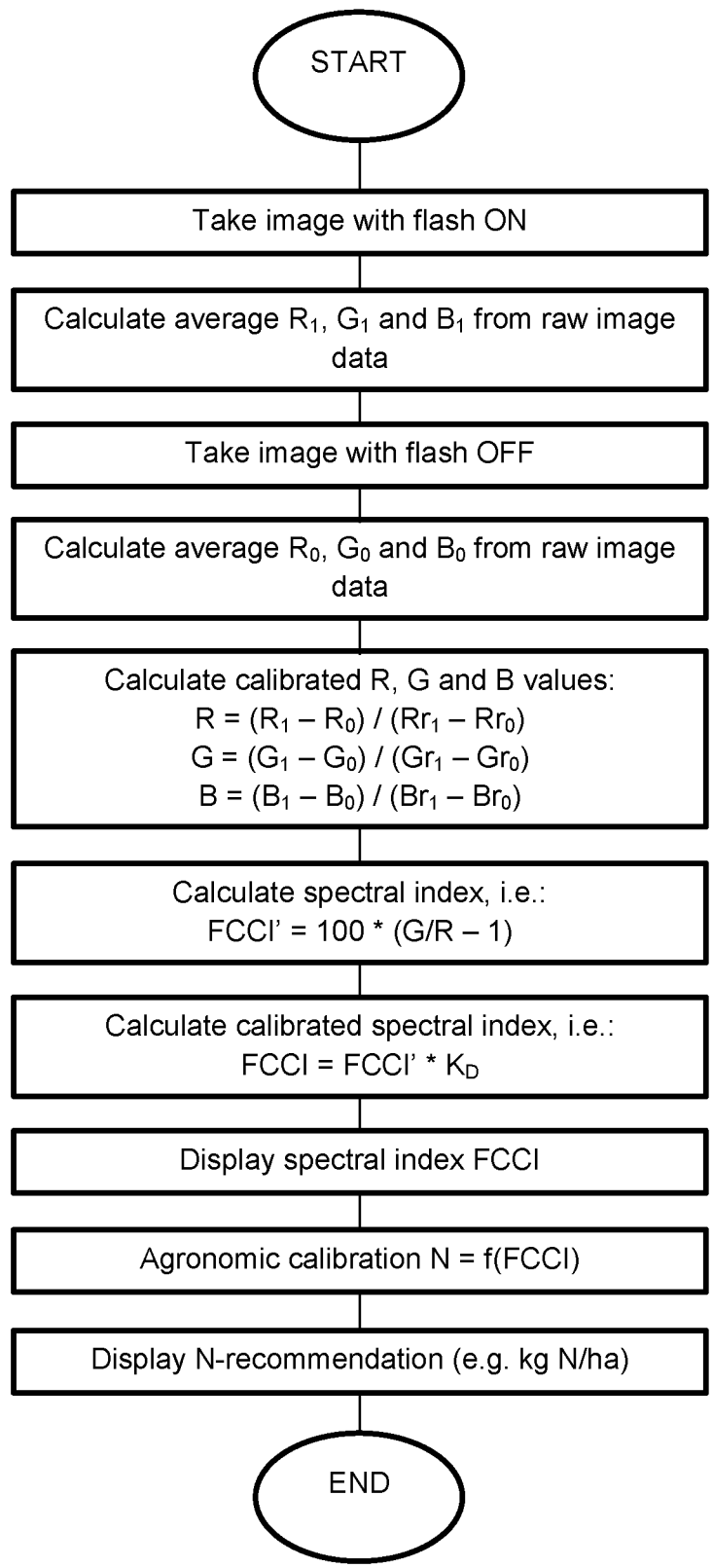
FIG. 5 shows an exemplary flow chart for carrying out a measurement procedure.

FIGS. 4A and 4B show a schematic representation of a light guide 8 that can be used in the examples of FIG. 1A, 1B, 1C, 2A, 2B, 2C or 3. FIG. 4A shows a cross sectional view. FIG. 4B shows a bottom view. In this example, the light guide 8 includes a light guide body 8a. In this example, the outer surface of the light guide body is provided with a, at least partially, light blocking layer 8b, such as a coating. The light blocking layer 8b includes a light-accepting window 8c, constructed as an aperture in the layer 8b. The light blocking layer 8b includes a light-emitting window 8d, constructed as an aperture in the layer 8b.

The light guide body 8a can be transparent. In this example, the light guide body 8a is translucent. Here, the light guide body 8a is constructed of a diffusively translucent material, such as an opal glass or opal plastic. The diffusively translucent material provides that light emitted at the light output window can be homogeneous. Thus, the light guide body 8a acts as a diffusor. It is also possible that alternatively, or additionally, the light guide includes one or more diffusively translucent surfaces, e.g. at the light input window 8c and/or at the light output window 8d, to act as diffusor.

EXPERIMENTAL

Figure 6:
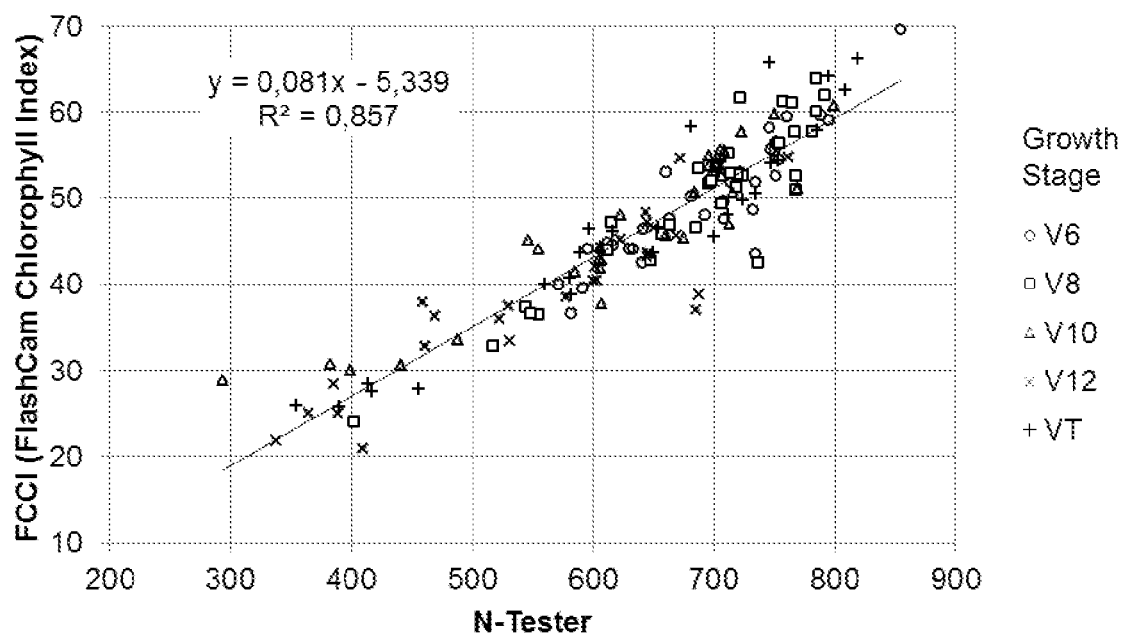
FIG. 6 shows a correlation graph for data recorded with the device according to the invention and a commercially available N-tester.

The performance of the device according to the invention was compared with the performance of a commercially available chlorophyll meter (Yara N-Tester, Yara International ASA, Norway). In the experiment, maize plants were grown at 5 different nitrogen levels. At 5 growth stages, individual leaves were picked and measured with both the chlorophyll meter and the device according to the invention. The results are shown in FIG. 6. A good correlation across growth stages was obtained with a coefficient of determination of $R^2=0.857$.

Herein, the invention is described with reference to specific examples of embodiments of the invention. It will, however, be evident that various modifications and changes may be made therein, without departing from the essence of the invention. For the purpose of clarity and a concise description features are described herein as part of the same or separate embodiments, however, alternative embodiments having combinations of all or some of the features described in these separate embodiments are also envisaged.

In the example, the processing unit controls the multi pixel digital colour sensor and the light source to take two consecutive images in response to a user activation. It will be appreciated that it is also possible that the processing unit controls the multi pixel digital colour sensor and the light source to take more than two images in response to a user activation. For example, the device can consecutively take images without-with-without the light source active. Starting a sequence with an image without illumination may help in synchronizing multi pixel digital colour sensor and light source for the image with light source illumination with, e.g. in devices that may have difficulties in synchronizing such as certain smartphones. The initial image without illumination may be discarded in the determination of the status of the plants. It is also possible that the process unit controls the multi pixel digital colour sensor and the light source to take a plurality of pairs of images in response to a single user command. For each pair of images, the status of the plants can be determined. The statuses of the plants for the consecutive pairs of images can e.g. be stored and/or averaged.

In the examples, the device is designed as a smartphone. It will be appreciated that the device can also be a dedicated handheld device. It is also possible that the device is designed as another handheld device such as a tablet, laptop, etc.

In the examples, the processing unit determines the value representative of a status of the plants for the entire image. It will be appreciated that the processing unit can also determine a value, representative of a status of the plants for one or more parts of the image.

In the examples, the processing unit determines the value representative of a status of the plants as a ratio of green and red image pixel intensities. It will be appreciated that also other mathematical combination of the available pixel intensities can be used.

In the examples, the processing unit determines a colour value representative of a difference in intensity values in the first and the second image for one or more colour components. It will be appreciated that it is also possible that the sample space is shielded from ambient light, e.g. by a skirt, clamp, or the like. When the sample space is sufficiently shielded from ambient light, obtaining the second image with the light emitter switched off may be omitted. Hence, then the colour value can be determined from the first image with the light emitter switched on only. However, other modifications, variations, and alternatives are also possible.

To conclude, the specifications, drawings and examples are, accordingly, to be regarded in an illustrative sense rather than in a restrictive sense.

For the purpose of clarity and a concise description features are described herein as part of the same or separate embodiments, however, it will be appreciated that the scope of the invention may include embodiments having combinations of all or some of the features described.

In the claims, any reference signs placed between parentheses shall not be construed as limiting the claim. The word 'comprising' does not exclude the presence of other features or steps than those listed in a claim. Furthermore, the words 'a' and 'an' shall not be construed as limited to 'only one', but instead are used to mean 'at least one', and do not exclude a plurality. The mere fact that certain measures are recited in mutually different claims does not indicate that a combination of these measures cannot be used to an advantage.

The invention claimed is:

1. A handheld device for determining a status of a plant comprising:
   a multi pixel digital colour sensor, configured for obtaining a colour image of a part of the plant which the status is to be determined, comprising at least a red (R), green (G) and blue (B) colour component, together forming a set of colour components;

a light source arranged for providing broadband illumination, wherein the light source and the multi pixel digital colour sensor are arranged in substantially a same plane;

a light guide for guiding the light from said light source into the direction of the multi pixel digital colour sensor;

a sample space, provided between the multi pixel digital colour sensor and a portion of the light guide, for insertion of at least a part of the plant which the status is to be determined, therein;

a processing unit configured for controlling at least the multi pixel digital colour sensor and the light source, characterised in that the processing unit is configured for:

switching the light source on and off, obtaining a first image of the part of the plant with the multi pixel digital colour sensor with the light source switched on and transmitting broadband illumination using the light guide through the part of the plant into the multi pixel digital colour sensor, obtaining a second image of the part of the plant with the multi pixel digital colour sensor, with the light source switched off and not illuminating the part of the plant, (i) determining a first colour value representative of a difference in intensity values in the first and the second image for a first of the colour components, (ii) determining a second colour value representative of a difference in intensity values in the first and the second image for a second of the colour components, (iii) calculating a value representative of the status of the plant using the first colour value and the second colour value.

2. The handheld device according to claim 1, wherein the device is a smartphone, a laptop or a tablet.

3. The handheld device according to claim 1, wherein the sample space is a slit.

4. The handheld device according to claim 1, wherein the sample space allows the insertion of an unprocessed part of the plant which the status is to be determined.

5. The handheld device according to claim 1, wherein the multi pixel digital colour sensor is selected from a CMOS image sensor and a CCD image sensor.

6. The handheld device according to claim 1, wherein the light source is a flash light of the handheld device.

7. The handheld device according to claim 1, wherein the light guide includes a light diffusor.

8. The handheld device according to claim 1, wherein the light guide is detachably attached to the handheld device.

9. The handheld device according to claim 1, wherein the light guide is part of a cover of the handheld device.

10. The handheld device according to claim 1, wherein the processing unit is further configured for determining a third colour value representative of a difference in intensity values in the first and the second image for a third of the colour components; and calculating the value representative of the status of the plant using the first colour value, the second colour value, and the third colour value.

11. The handheld device according to claim 1, wherein the processing unit is configured for, in step (iii), calculating said value representative of the status of the plant based on a ratio of the first colour value and the second colour value.

12. The handheld device according to claim 1, wherein the processing unit is configured for calibrating the first colour value and the second colour value.

13. The handheld device according to claim 1, wherein the processing unit is configured to use at least one colour component that is less sensitive to changes in the status of the plant than the other of the colour components.

14. The handheld device according to claim 1, wherein the processing unit is configured for obtaining the first and second image in response to a single user command.

15. The handheld device according to claim 1, the device further comprising a communications unit configured for communicating the determined status of the plant, or a parameter derived therefrom, to an applicator system.

16. A method for determining the status of a plant using the handheld device as defined in claim 1, the method including:

obtaining, using the multi pixel digital colour sensor, the first image of the part of the plant while the light source is switched on and transmits the broadband illumination through the part of the plant onto the multi pixel digital colour sensor, obtaining, using the multi pixel digital colour sensor, the second image of the part of the plant while the light source is switched off and does not illuminate the part of the plant, and calculating the status of the plant by having the processing unit:

(i) determine the first colour value representative of the difference in intensity values in the first and the second image for the first of the colour components;

(ii) determine the second colour value representative of the difference in intensity values in the first and the second image for the second of the colour components; and (iii) calculate the value representative of the status of the plant using the first colour value and the second colour value.

17. The method according to claim 16 including taking an action, as the action being one of watering, fertilizing, harvesting, shielding, ventilating, or heating, on a basis of the value calculated in step (iii).

18. The method according to claim 16, wherein the part of the plant is a leaf or a part thereof.

19. The handheld device according to claim 7, wherein the light diffusor is manufactured from a diffusively translucent material.

20. The handheld device according to claim 15, wherein the applicator system is one of a fertilization, fertigation, or watering system.

21. The handheld device according to claim 1, wherein the sample space is an open sample space in contact with ambient air and ambient light.

* * * * *